US009804243B2

United States Patent
Kitane et al.

(10) Patent No.: US 9,804,243 B2
(45) Date of Patent: Oct. 31, 2017

(54) MAGNETIC RESONANCE IMAGING APPARATUS

(71) Applicant: TOSHIBA MEDICAL SYSTEMS CORPORATION, Otawara-Shi, Tochigi-Ken (JP)

(72) Inventors: Shinichi Kitane, Nasushiobara (JP); Masashi Ookawa, Otawara (JP); Kazuhiro Sueoka, Nasushiobara (JP)

(73) Assignee: TOSHIBA MEDICAL SYSTEMS CORPORATION, Otawara-Shi, Tochigi-Ken (JP)

( * ) Notice: Subject to any disclaimer, the term of this patent is extended or adjusted under 35 U.S.C. 154(b) by 699 days.

(21) Appl. No.: 14/259,670

(22) Filed: Apr. 23, 2014

(65) Prior Publication Data
US 2014/0232405 A1    Aug. 21, 2014

Related U.S. Application Data

(63) Continuation of application No. PCT/JP2013/083595, filed on Dec. 16, 2013.

(30) Foreign Application Priority Data

Dec. 20, 2012  (JP) ................................ 2012-278381

(51) Int. Cl.
   *G01R 33/56*  (2006.01)
   *A61B 5/055*  (2006.01)
   (Continued)

(52) U.S. Cl.
   CPC ............ *G01R 33/56* (2013.01); *A61B 5/0037* (2013.01); *A61B 5/055* (2013.01); *G01R 33/38* (2013.01)

(58) Field of Classification Search
   CPC .............................. G01R 33/302; G01R 33/60
   See application file for complete search history.

(56) References Cited

U.S. PATENT DOCUMENTS 6,147,493 A * 11/2000 Miyoshi ........... G01R 33/56509
                                                        324/306
7,298,146 B1 * 11/2007 Maier ................ G01R 33/5617
                                                        324/307

(Continued)

FOREIGN PATENT DOCUMENTS

JP       04-071535        3/1992
JP       2005-40416       2/2005
(Continued)

OTHER PUBLICATIONS

JP Office Action dated Aug. 2, 2016 in JP 2012-278381.
(Continued)

*Primary Examiner* — Gregory H Curran
(74) *Attorney, Agent, or Firm* — Nixon & Vanderhye P.C.

(57) ABSTRACT

A magnetic resonance imaging apparatus of an embodiment includes: an imaging condition setting section configured to set an imaging condition for a main scan, a preparatory scan performing section configured to repeat a preparatory scan to be performed by the use of the imaging condition for a main scan and a changeably inputted center frequency so as to generate a preparatory image in real time, a display section on which the preparatory image can be displayed in real time, an optimum center frequency setting section configured to change the center frequency so as to change a situation in which a banding artifact appears and configured to set an optimum center frequency according to a user operation based on an observation of the preparatory image, and a main scan performing section configured to reconstruct an image for a diagnosis by using the optimum center frequency having been set.

11 Claims, 12 Drawing Sheets

(51) Int. Cl.
*A61B 5/00* (2006.01)
*G01R 33/38* (2006.01)

(56) References Cited

U.S. PATENT DOCUMENTS

| | | |
|---|---|---|
| 2005/0068029 A1 | 3/2005 | Asano |
| 2005/0165295 A1 | 7/2005 | Li et al. |
| 2011/0006767 A1* | 1/2011 | Sack ..................... A61B 5/055 324/309 |

FOREIGN PATENT DOCUMENTS

| | | |
|---|---|---|
| JP | 2005-95416 | 4/2005 |
| JP | 2008-200508 | 9/2008 |
| JP | 2011-167559 | 9/2011 |

OTHER PUBLICATIONS

English Translation of International Preliminary Report on Patentability dated Jun. 23, 2015 for Application No. PCT/JP2013/083595.

Shigematsu et al., "Comparison of 3D time-of-flight turbo MR angiography with conventional 3D-FISP MR angiography; experimental and clinical evaluation for the intracranial arteries", Proc. Intl. Soc. Mag. Reson, Med., 6, 1998, 05, #1282.

International Search Report for PCT/JP2013/083595 dated Feb. 18, 2014.

\* cited by examiner

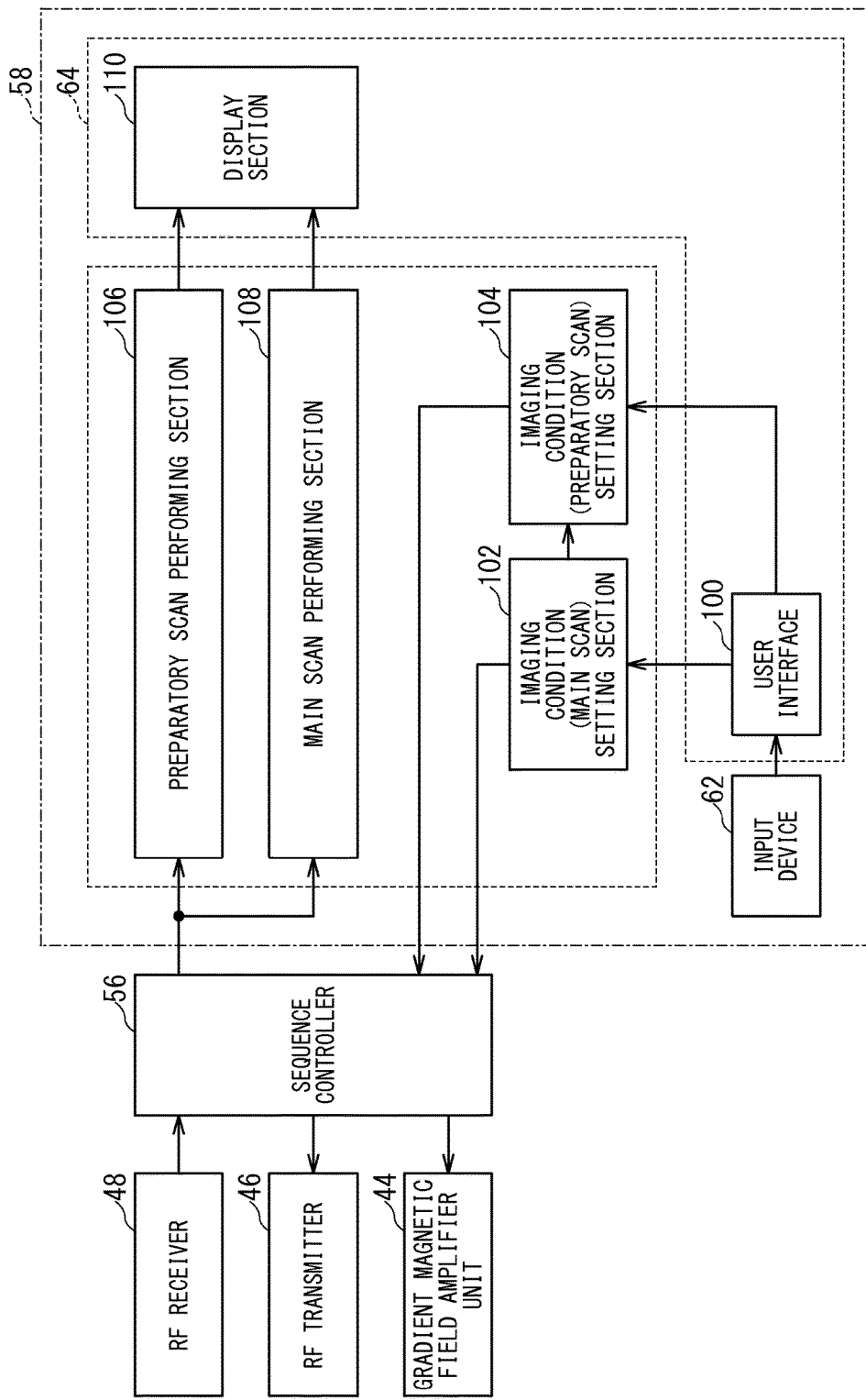

MAGNETIC RESONANCE IMAGING APPARATUS

CROSS-REFERENCE TO RELATED APPLICATIONS

This application is a Continuation Application of No. PCT/JP2013/83595, filed on Dec. 16, 2013, and the PCT application is based upon and claims the benefit of priority from Japanese Patent Applications No. 2012-278381 filed on Dec. 20, 2012, the entire contents of which are incorporated herein by reference.

FIELD

An embodiment of the present invention relates to a magnetic resonance imaging apparatus.

BACKGROUND

A magnetic resonance imaging apparatus is an apparatus configured to excite a nuclear spin of a test object put in a static magnetic field by an RF (radio frequency) signal of a Larmor frequency, and to reconstruct a magnetic resonance signal generated by the test object as the test object is excited so as to generate an image.

A magnetic resonance imaging apparatus of a high static magnetic field strength, e.g., 3 T (Tesla) recently comes into wide use. A raised static magnetic field strength increases an SNR. Then, space or time resolution enhanced by an advantage of a high SNR is expected.

In the meantime, the raised static magnetic field strength is accompanied by growth in unevenness of the static magnetic field. A method called SSFP (Steady State Free Precession) is particularly sensitive to the unevenness of the static magnetic field. An imaging operation using an SSFP method has a problem of a band-shaped artifact called a banding artifact, e.g., as disclosed in Japanese Unexamined Patent Publication No. 2011-167559.

The SSFP method is doomed to suffer a phase mismatch in a pixel in the presence of unevenness of the magnetic field. Although a slight phase mismatch causes no significant problem, the phase mismatch enlarges if unevenness of the magnetic field enlarges as the magnetic field strength increases. If the phase mismatch reaches 180 degrees, positive and negative signals cancel each other resulting in a relevant displayed pixel looking black. This phenomenon is typically called a banding artifact which undesirably appears on an image. The banding artifact takes a form of band-shaped artifacts appearing periodically in space, where an appearance interval broadens as a repetition period of time (TR interval) of an excitation RF pulse shortens, and conversely narrows as the repetition period of time TR lengthens.

One method for reducing the banding artifact is to shift a center frequency F0. The banding artifact appears where the phase mismatch is 180 degrees. Thus, conditions of the phase mismatch can be changed by means of a shift in the center frequency F0. If the conditions of the phase mismatch change, a position at which a banding artifact appears on the image shifts correspondingly to that change.

For capturing an image of the heart, a banding artifact appearing at a position excepting the heart is not a significant problem. Meanwhile, a targeted region of interest (ROI) such as the heart is not very large. Thus, a shift in the center frequency F0 for changing the position of appearance of the banding artifact can make it possible to avoid a bad influence on the image of the heart. A center frequency F0 at which an influence of the banding artifact can be avoided is called an "optimum F0", hereafter.

The influence of the unevenness of the static magnetic field differs on a patient-by-patient basis, and differs depending upon a position or orientation of an imaging cross section even of one and the same patient. Thus, a usual practice is to have a preparatory scan to search for an optimum F0 before and independently of a main scan (a scan for capturing an originally intended image) in order to search for an optimum F0 for every patient.

Imaging conditions for a preparatory scan are ordinarily set for the preparatory scan to search for an optimum F0 separately from imaging conditions for a main scan. An operation load for the preparatory scan is so large to take time. Further, an ordinary practice of the preparatory scan is such that a user determines an optimum F0 from images less affected by the banding artifact while manually changing and displaying plural images obtained in the preparatory scan. Then, the user sets the optimum F0 as one of imaging conditions for a main scan on another occasion of starting the main scan. Thus, it takes time to determine the optimum F0, and it takes time for an operation to reflect the optimum F0 on the main scan as well.

In order to solve the above problems, a magnetic resonance imaging apparatus by which an optimum F0 for avoiding a banding artifact can be efficiently determined with a small operation load is demanded.

SUMMARY

A magnetic resonance imaging apparatus of an embodiment includes: an imaging condition setting section configured to set an imaging condition for a main scan for obtaining an image for a diagnosis, a user interface via which a center frequency can be changeably inputted in real time; a preparatory scan performing section configured to repeat a preparatory scan to be performed by the use of the imaging condition having been set and the center frequency changeably inputted in real time, the preparatory scan performing section being configured to reconstruct data acquired in the preparatory scan in real time so as to generate a preparatory image, a display section on which the preparatory image can be displayed in real time, an optimum center frequency setting section configured to change the center frequency according to a user operation via the user interface so as to change a situation in which a banding artifact appears, the optimum center frequency setting section being configured to set an optimum center frequency according to a user operation based on an observation of the preparatory image, and a main scan performing section configured to perform the main scan by using the optimum center frequency having been set and the imaging condition for the main scan having been set so as to reconstruct the image for a diagnosis.

BRIEF DESCRIPTION OF DRAWINGS

FIG. 2 is a block diagram which depicts an exemplary functional setup related particularly to data processing for avoiding a banding artifact in a functional setup of the magnetic resonance imaging apparatus of the embodiment;

FIGS. 3A to 3B are a first diagrams which schematically illustrate banding artifacts that the magnetic resonance imaging apparatus of the embodiment deals with;

FIGS. 4A to 5D are a second diagrams which schematically illustrate banding artifacts that the magnetic resonance imaging apparatus of the embodiment deals with;

FIG. 5 is a flowchart which illustrates an exemplary operation related to avoidance of banding artifacts (first embodiment);

DESCRIPTION OF EMBODIMENTS

An embodiment of the invention will be explained below on the basis of the drawings.

(1) Setup and Overall Operation

Figure 1:
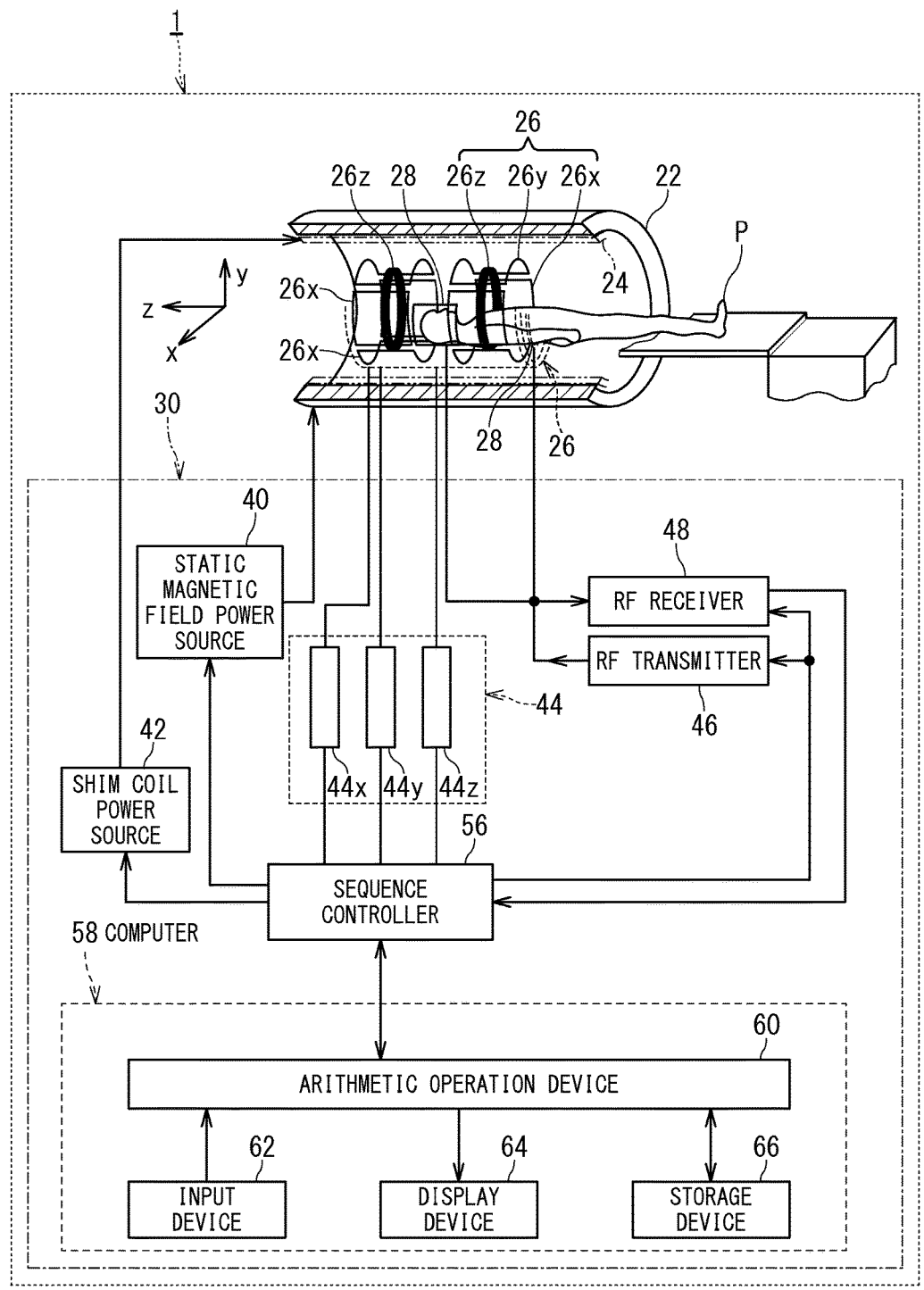
FIG. 1 is a block diagram which depicts an overall setup of a magnetic resonance imaging apparatus of an embodiment.

FIG. 1 is a block diagram which depicts an overall setup of a magnetic resonance imaging apparatus 1 of the embodiment. As depicted in FIG. 1, the magnetic resonance imaging apparatus 1 has a cylindrical magnet for static magnetic fields 22 which forms a static magnetic field, a cylindrical shim coil 24 provided coaxially with and inside the magnet for static magnetic fields 22, a gradient magnetic field coil 26, a signal transmission/receiving coil for the whole body 28, a control system 30, a bed on which a test object (patient) P can be mounted, etc. Further, the magnetic resonance imaging apparatus 1 has one or a plurality of receiving coils (not depicted) in addition to the signal transmission/receiving coil for the whole body 28. Still further, the control system 30 has a static magnetic field power source 40, a shim coil power source 42, a gradient magnetic field amplifier unit 44, an RF transmitter 46, an RF receiver 48, a sequence controller 56, a computer 58, etc. Further, the computer 58 has an arithmetic operation device 60, an input device 62, a display device 64, a storage device 66, etc., as internal components.

The magnet for static magnetic fields 22 is coupled with the static magnetic field power source 40, and forms a static magnetic field in imaging space by means of a current supplied by the static magnetic field power source 40. The shim coil 24 is coupled with the shim coil power source 42, and levels the static magnetic field off by means of a current supplied by the shim coil power source 42. The magnet for static magnetic fields 22 is formed by a superconductive coil in lots of cases, and is coupled with the static magnetic field power source 40 so as to be supplied with a current in case of being excited. Once being excited, the magnet for static magnetic fields 22 is decoupled in general. Incidentally, the magnet for static magnetic fields 22 may be formed by a permanent magnet without being provided with the static magnetic field power source 40.

The gradient magnetic field coil 26 has an X-axis gradient magnetic field coil 26x, a Y-axis gradient magnetic field coil 26y and a Z-axis gradient magnetic field coil 26z. The gradient magnetic field coil 26 is shaped like a cylinder inside the magnet for static magnetic fields 22.

The magnet for static magnetic fields 22, the shim coil 24, the gradient magnetic field coil 26, the signal transmission/receiving coil for the whole body 28 and so on are contained in a frame 200 having a cylindrical imaging space.

The gradient magnetic field amplifier unit 44 is formed by an X-axis gradient magnetic field amplifier unit 44x, a Y-axis gradient magnetic field amplifier unit 44y and a Z-axis gradient magnetic field amplifier unit 44z. The X-axis gradient magnetic field coil 26x, the Y-axis gradient magnetic field coil 26y and the Z-axis gradient magnetic field coil 26z are coupled with the X-axis gradient magnetic field amplifier unit 44x, the Y-axis gradient magnetic field amplifier unit 44y and the Z-axis gradient magnetic field amplifier unit 44z, respectively.

The RF transmitter 46 generates an RF pulse of a Larmor frequency for causing a nuclear magnetic resonance on the basis of control information provided by the sequence controller 56, and provides the signal transmission/receiving coil for the whole body 28 (WBC: Whole Body Coil) with the RF pulse. If the signal transmission/receiving coil for the whole body 28 transmits an RF pulse to a test object (patient), the test object generates an MR signal, and the signal transmission/receiving coil for the whole body 28 receives the MR signal.

The MR signal received by the signal transmission/receiving coil for the whole body 28 is provided to the RF receiver 48 via a signal cable. Further, an MR signal received by a receiving coil 120 provided close to the test object P is provided to the RF receiver 48, as well, via a signal cable.

The RF receiver 48 carries out various kinds of data processing such as pre-amplification, intermediate frequency conversion, phase detection, baseband frequency amplification, filtering and so on for the received MR signal, and then A/D (analog to digital)-converts the MR signal so as to generate raw data which is digitized complex data. The RF receiver 48 provides the sequence controller 56 with the generated raw data of the MR signal.

The sequence controller 56 generates a data sequence and control information for generating gradient magnetic fields Gx, Gy and Gz and an RF pulse which correspond to imaging conditions including a pulse sequence having been set as controlled by the arithmetic operation device 60 in the computer 58, and provides the respective gradient magnetic field amplifier units 44x, 44y and 44z and the RF transmitter 46 with what is generated.

Further, the sequence controller 56 is provided by the RF receiver 48 with an MR signal received in response to the gradient magnetic fields Gx, Gy and Gz and the RF pulse as raw data, and outputs the raw data to the arithmetic operation device 60.

The arithmetic operation device 60 controls the magnetic resonance imaging apparatus 1 entirely, and in addition sets or changes imaging conditions including various kinds of pulse sequences on the basis of information having been provided to the input device and variously set by a user's operation, and controls the sequence controller 56 on the basis of the imaging conditions having been set or changed. Further, the arithmetic operation device 60 carries out a reconstruction process including inverse Fourier transform, etc., for the raw data provided by the sequence controller 56 so as to generate image data.

The arithmetic operation device 60 in the computer 58 is formed by having a processor, etc., and implements the respective functions described above and respective functions which will be explained below by running program codes stored in the storage device 66.

(2) Functional Setup for Avoiding Banding Artifact

FIG. 2 is a block diagram which depicts an exemplary functional setup related particularly to data processing for avoiding a banding artifact in the functional setup of the magnetic resonance imaging apparatus 1 of the embodiment.

The magnetic resonance imaging apparatus 1 of the embodiment has a user interface 100, an imaging condition (main scan) setting section 102, an imaging condition (preparatory scan) setting section 104, a preparatory scan performing section 106, a main scan performing section 108, a display section 110 and so on as components for the functions described above to be implemented on the computer 58. These functions are implemented, e.g., by the processor that the arithmetic operation device 60 in the computer 58 has running a certain program code, and in addition can be implemented by means of a hardware component or of a combination of software and hardware components.

The user interface 100 is used for setting various data including imaging conditions, instruction data, etc., to the apparatus on the basis of input data entered on the input device 62 formed by a mouse, a keyboard, etc., while using an input screen displayed on the display device 64.

The imaging condition (main scan) setting section 102 sets various kinds of data related to a pulse sequence in the main scan and data related to an imaging cross section, resolution, etc., of an image to be captured in the main scan as imaging conditions on the basis of various kinds of data inputted through the user interface 100. The main scan means a scan for obtaining a diagnosis image.

The imaging conditions having been set for the main scan are provided to the sequence controller 56, and are rendered pieces of fundamental information for determining a parameter of an RF pulse for the RF transmitter 46 and a parameter of a gradient magnetic field for the gradient magnetic field amplifier unit 44. Further, the main scan performing section 108 is provided, as well, with the imaging conditions set by the imaging condition (main scan) setting section 102.

Meanwhile, the imaging condition (preparatory scan) setting section 104 sets the imaging conditions set by the imaging condition (main scan) setting section 102 as they are with some exceptions as imaging conditions for a preparatory scan. Major one of the above exceptions mentioned here is a center frequency of an RF pulse in the preparatory scan.

The user interface 100 is configured, as well, to change the center frequency of the RF pulse in the preparatory scan in real time as described later.

Then, the imaging condition (preparatory scan) setting section 104 sets data of the center frequency that the user changes in real time as the center frequency of the RF pulse in the preparatory scan, and provides the RF transmitter 46 with the center frequency via the sequence controller 56.

The preparatory scan performing section 106 performs preparatory scans continuously and repeatedly by using the data of the center frequency that the user changes in real time and the imaging conditions other than the center frequency set by the imaging condition (main scan) setting section 102. Then, the preparatory scan performing section 106 reconstructs data acquired in the preparatory scan in real time so as to generate a preparatory image.

The generated preparatory image is displayed in real time on the display section 110 which presents the image to the user. If the user changes the center frequency, a position where a banding artifact appears changes as described later, and a situation in which the banding artifact is put apart from a region of interest (ROI) is observed on the preparatory image displayed on the display section 110. If the user performs a certain operation, e.g., to end the preparatory scan in that condition, the center frequency at that moment is set onto the imaging condition (main scan) setting section 102 as an optimum center frequency.

Then, the main scan performing section 108 performs a main scan by using the optimum center frequency set above and the imaging conditions for the main scan having been set in advance, and reconstructs an image for a diagnosis in which the banding artifact is put apart so as to provide the display section 110 with the image.

FIGS. 3A-3B and 4A-4D each schematically illustrate how the magnetic resonance imaging apparatus 1 of the embodiment deals with a banding artifact.

The banding artifact is an artifact which appears mostly in an image captured by the use of the SSFP method and is caused by unevenness of a magnetic field as previously described. As exemplarily depicted in FIGS. 3A and 3B, band-shaped artifacts (banding artifacts) periodically appear in a field of view (FOV). A banding artifact put on top of a region of interest (ROI) such as the heart, if any, obstructs an imaging diagnosis.

Figure 3A:
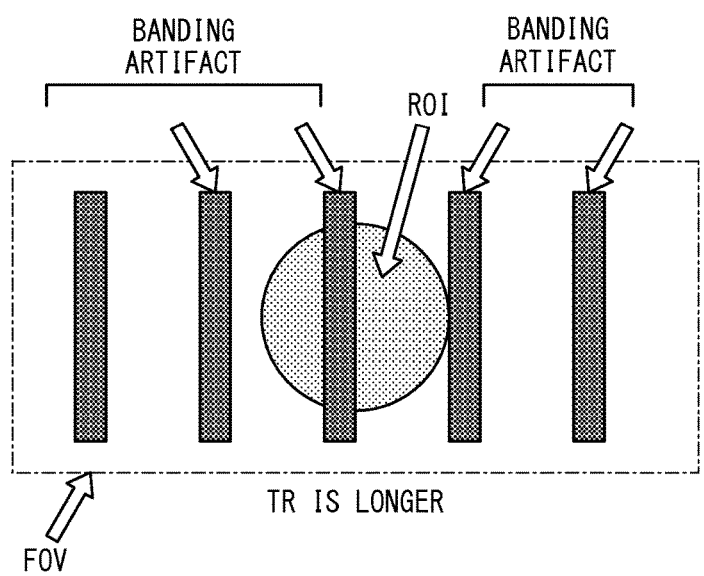
Figure 3B:
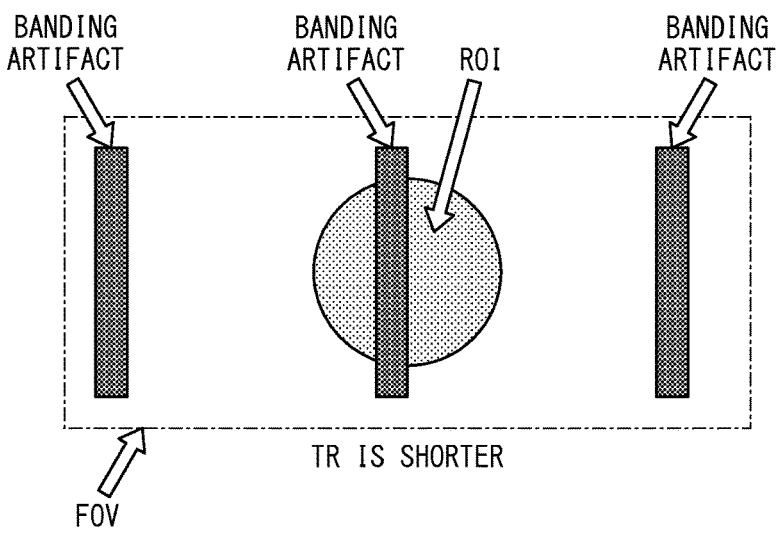

A period of appearance between banding artifacts (i.e., an interval of generated banding artifacts) depends upon a repetition period of time TR of an excitation pulse. The longer the repetition period of time TR is, the shorter the interval between banding artifacts is (FIG. 3A). Conversely, the shorter the repetition period of time TR is, the longer the interval between banding artifacts is (FIG. 3B).

A longer interval between banding artifacts causes the banding artifact to be put on top of the ROI less probably, and thus it is advantageous to set a repetition period of time TR as short as possible from a viewpoint of avoidance of banding artifacts.

Figure 4A:
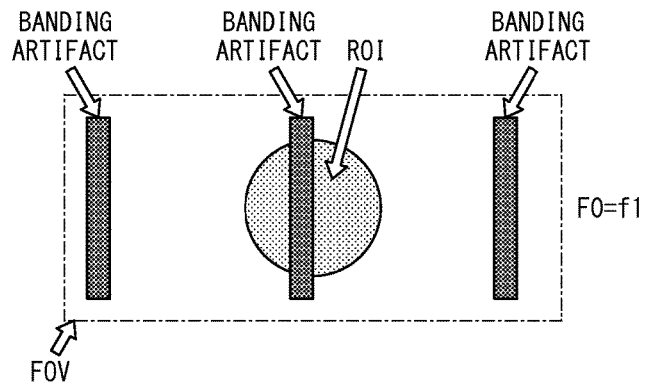
Figure 4B:
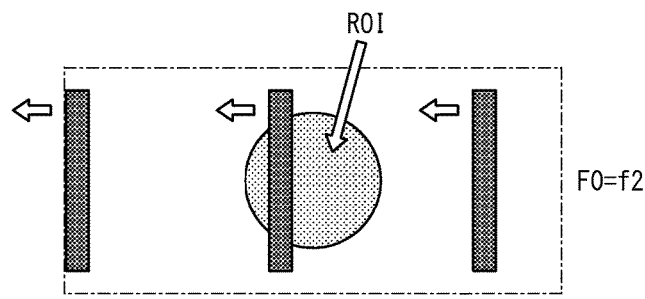
Figure 4C:
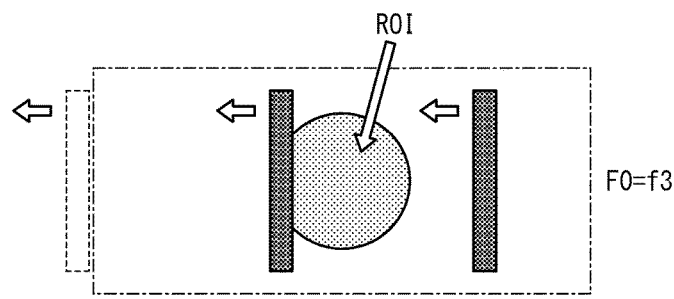
Figure 4D:
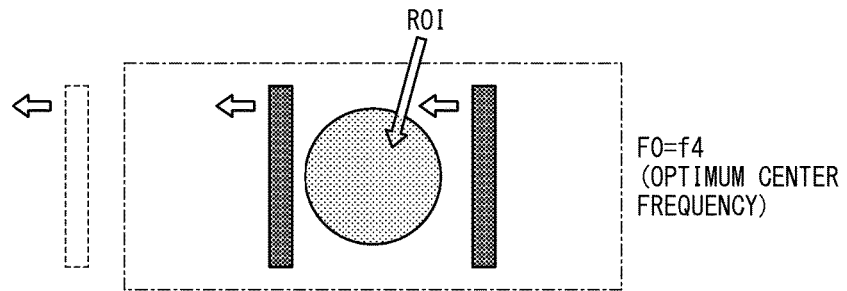

As exemplarily depicted in FIGS. 4A-4D, meanwhile, positions where banding artifacts appear shift as a center frequency F0 of a transmission RF wave is shifted. Thus, even if a banding artifact is put on top of the ROI, the banding artifact can be put apart from the ROI so that they do not overlap as depicted in FIG. 4D if the center frequency is shifted by a proper value.

According to the embodiment, while changing the center frequency in real time, a user observes a preparatory image captured on the center frequency having been changed so that the user can easily find out a center frequency causing no overlap between banding artifacts and the ROI.

An operation of the magnetic resonance imaging apparatus 1 related to avoidance of banding artifacts of the embodiment will be specifically explained below.

(3) Operation Related to Avoidance of Banding Artifacts (First Embodiment)

Figure 5:
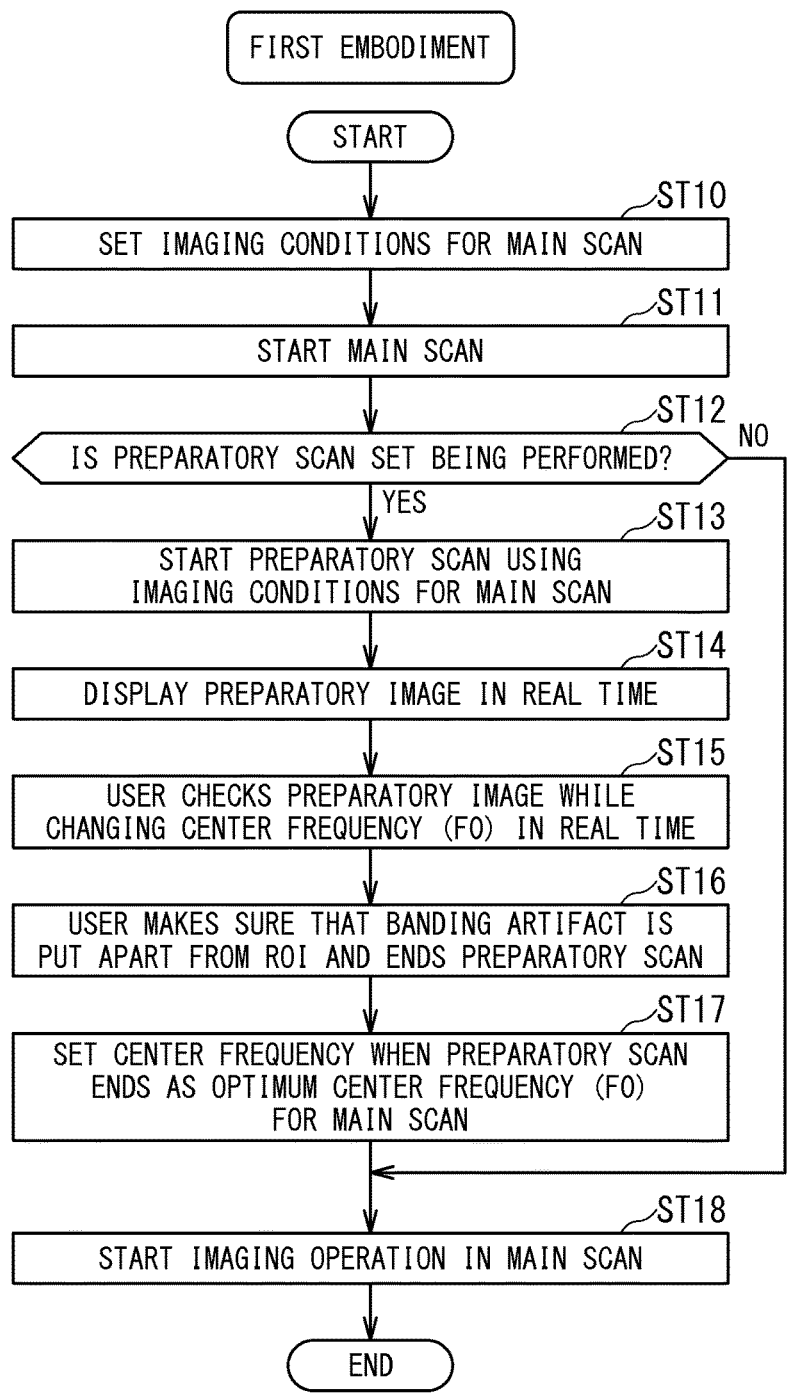

FIG. 5 is a flowchart which illustrates an exemplary operation related to avoidance of banding artifacts (first embodiment). Further, FIG. 6 exemplarily depicts the user interface 100 and a preparatory image displayed on the display section 110.

Figure 6:
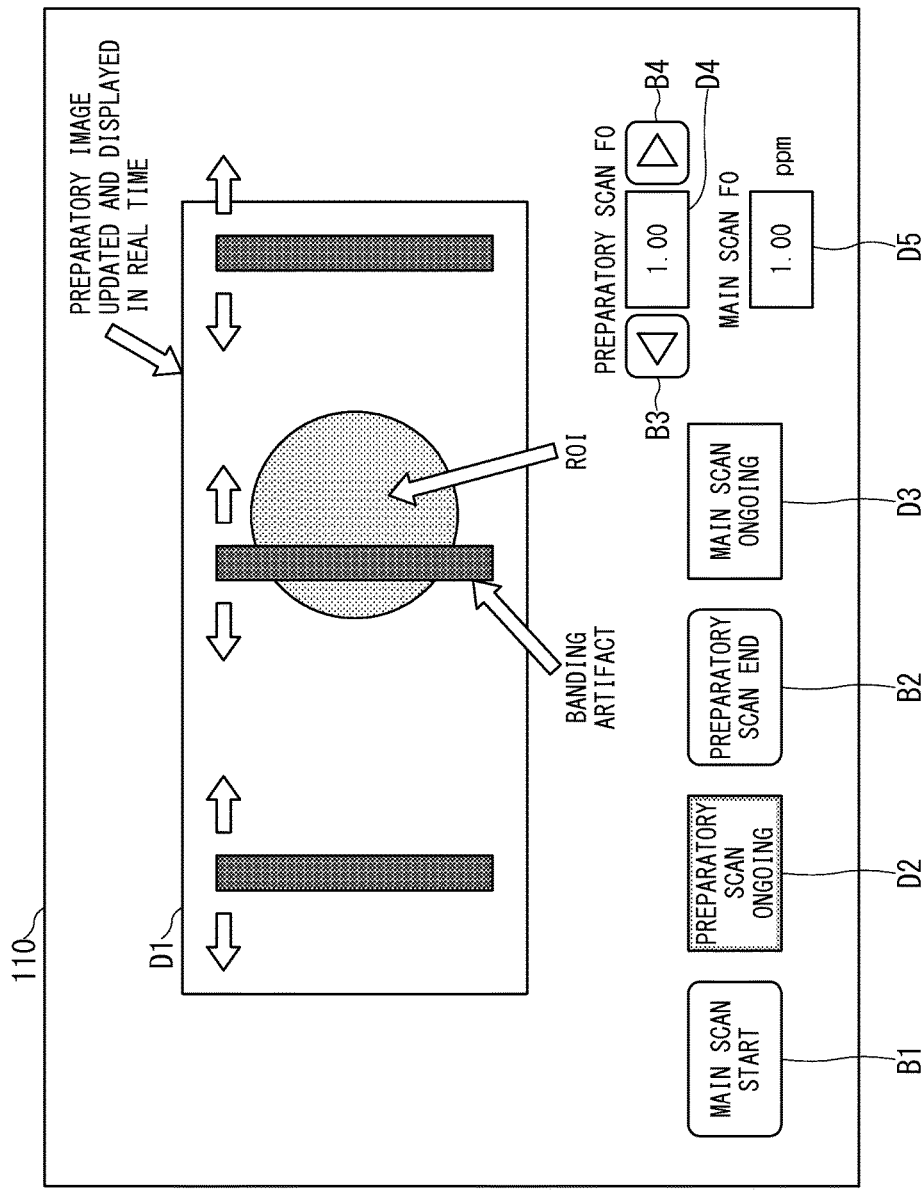
FIG. 6 depicts user interface and an exemplary preparatory image displayed on a display section.

As depicted in FIG. 6, the display section 110 has a display area D1 on which a preparatory image is displayed in real time, and in addition, a "main scan start" button B1, a "preparatory scan ongoing" indication D2, a "preparatory scan end" button B2, a "main scan ongoing" indication D3, a "center frequency downshift" button B3, a "center frequency upshift" button B4, a "center frequency in preparatory scan" indication D4, a "center frequency in main scan" indication D5 and so on.

The exemplary operation of the first embodiment will be explained with reference to FIGS. 5 and 6.

First of all, set imaging conditions for a main scan at a step ST10. The imaging conditions include a pulse sequence type of the SSFP method, etc., various parameters related to the pulse sequence such as a repetition period of time of an excitation pulse TR, etc., a center frequency of transmission (initial value), a parameter related to a position, orientation, thickness, etc., of an imaging cross section, a parameter related to a position or size of the FOV, a parameter related to resolution such as a matrix size, etc. Set these imaging conditions via a user interface which is not depicted. In addition, the step ST10 includes a setting to decide whether a preparatory scan is performed before an imaging operation in a main scan. As a preparatory scan is performed while the center frequency F0 is being changed according to the embodiment, the preparatory scan is called an F0 preparatory scan (or F0-prepscan).

If the imaging conditions for a main scan are completely set, a user operation to start a main scan is done at a step ST11 (step ST11). For instance, the "main scan start" button B1 is clicked.

Upon receiving a signal of the operation, decide at a step ST12 whether an F0 preparatory scan is set being performed. Unless an F0 preparatory scan is set being performed, go to a step ST18 so as to start a main scan according to the imaging conditions having been set. If an F0 preparatory scan is set being performed, on the other hand, go to a step ST13 so that an F0 preparatory scan using the imaging conditions having been set for a main scan is started.

Specifically, an F0 preparatory scan using same parameters as those of the pulse sequence type, the repetition period of time TR, the imaging cross section and the resolution having been set for a main scan is started. Further, the F0 preparatory scan is started by the use of the initial value having been set to the center frequency. If the F0 preparatory scan is started, the "preparatory scan ongoing" indication D2 is highlighted as exemplarily depicted in FIG. 6.

Data processing to reconstruct MR signals acquired in the F0 preparatory scan is run in real time, and a preparatory image generated by the reconstructing data processing is displayed on the preparatory image display area D1 in real time as depicted in FIG. 6 (step ST14). That is, in the F0 preparatory scan, so called cine imaging is performed for a desired ROI such as a heart.

Figure 7A:
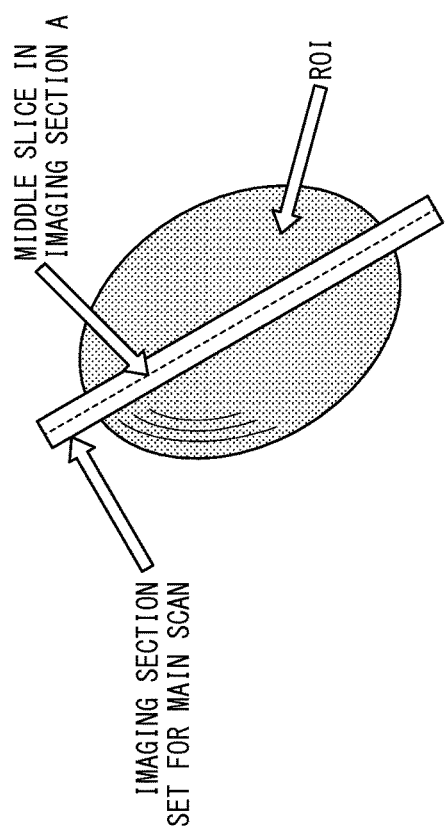
FIGS. 7A to 7B illustrate a relationship between an imaging cross section set a main scan and a slice plane set for an F0 preparatory scan.
Figure 7B:
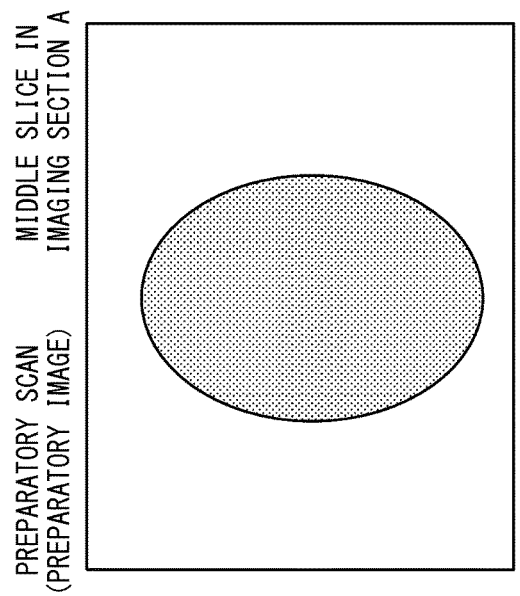

The F0 preparatory scan requires rapidity. Thus, if the imaging cross sect ion set for a main scan is a slab having a thickness as exemplarily depicted in FIG. 7A, a 2D image on a slice plane in the middle of the slab only is captured in the F0 preparatory scan as depicted in FIG. 7B. Although a situation in which banding artifacts appear differs if the position or orientation of the imaging cross section significantly differs, the situation in which banding artifacts appear hardly change in the same imaging cross section (slab). Thus, a real time feature of the F0 preparatory scan is achieved by 2D imaging only on the slice plane in the middle of the slab. In a case, if any, where the imaging cross section is set for the main scan not as a slab having a thickness but as a plurality of slices, the middle one of the slices is set as a slice for the F0 preparatory scan.

If the user clicks the "center frequency downshift" button B3 or the "center frequency upshift" button B4, the center frequency F0 of the F0 preparatory scan leaves the initial value and shifts upwards or downwards.

Then, a position where a banding artifact appears changes correspondingly to the shift of the center frequency F0, as depicted in FIGS. 4A to 4D. The user resultantly can, while changing the center frequency F0 in real time, check how a banding artifact which appears on the preparatory image in the F0 preparatory scan changes in real time (step ST15).

A shift value of the center frequency F0 in the F0 preparatory scan is indicated in the "center frequency in preparatory scan" indication D4 as, e.g. a value of change relative to the initial value (in ppm: parts per million). The shift value changes more or less in a width of plus/minus 1 ppm.

The user checks how a banding artifact appears on the preparatory image while changing the center frequency F0, and finds out a situation including no overlap between the banding artifact and the ROI. The then center frequency F0 is the optimum center frequency F0 on which banding artifacts are put apart from the ROI.

Upon finding out the optimum center frequency F0 in this way, the user clicks the "preparatory scan end" button B2. The apparatus ends the preparatory scan at that moment according to the operation signal (step ST16).

The center frequency F0 when the preparatory scan ends is set as an optimum center frequency F0$opt$ at the same time (step ST17). That is, among the imaging conditions of the main scan set at the step ST10, only the center frequency F0 (initial value) is replaced with the optimum center frequency F0$opt$. Then, an imaging operation in the main scan is started under the imaging conditions (step ST18).

According to the magnetic resonance imaging apparatus 1 of the first embodiment described above, a preparatory image on which the center frequency F0 that a user changes in real time is reflected is displayed in real time. Thus, the user can find out the optimum center frequency F0$opt$ causing no overlap between banding artifacts and the ROI briefly with a simple operation by observing the preparatory image.

Further, as the F0 preparatory scan is automatically started by the operation to start a main scan and the imaging conditions set for the main scan are automatically, and substantially as they are, applied and set to the imaging conditions for the F0 preparatory scan, no user operation is needed for the F0 preparatory scan.

Still further, after the optimum center frequency F0$opt$ is found out in the F0 preparatory scan, the optimum center frequency F0$opt$ is set as one of the imaging conditions for a main scan only by a simple operation to end the F0 preparatory scan, and the F0 preparatory scan can be automatically changed to the main scan.

(3-1) First Modification of First Embodiment

The F0 preparatory scan is a scan to search for an optimum center frequency F0$opt$ for avoiding a banding artifact in the main scan, and it is thus preferable to have the F0 preparatory scan in imaging conditions as identical as possible to those for the main scan. In particular, it is preferable to apply the same resolution to the F0 preparatory scan and to the main scan.

Figure 8:
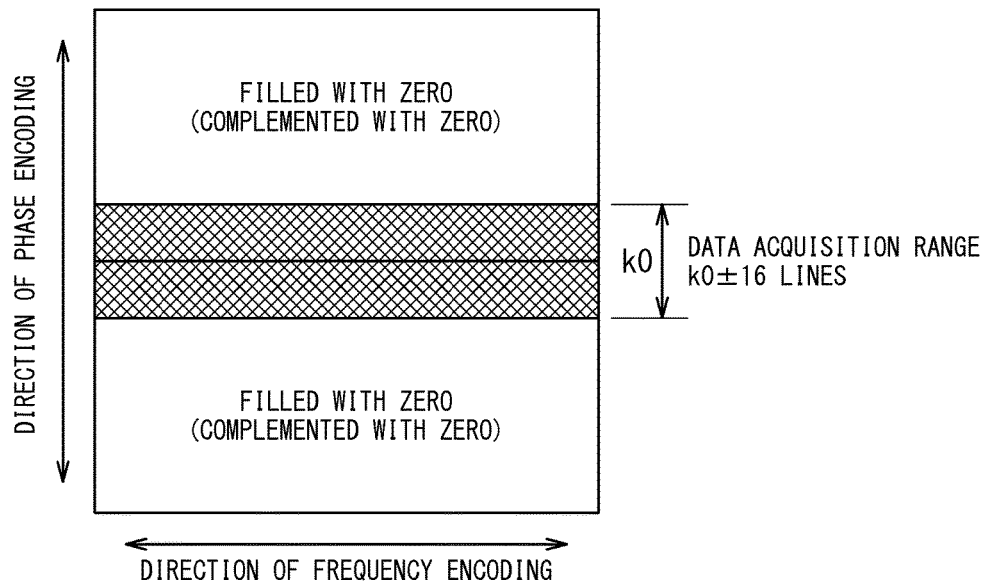
FIG. 8 illustrates an operation of a first modification of the first embodiment.

Meanwhile, the F0 preparatory scan needs to be performed rapidly in order that the preparatory image is generated in real time. According to a first modification of the first embodiment, then, while acquiring MR signals only in a certain range centered at a phase encoding quantity of zero (k0), perform data processing to complement zero (zero filling) for a range excepting the above certain range, render a phase encoding number same as that of the main scan and perform a reconstruction process as depicted in FIG. 8.

If, e.g., a phase encoding line number is 128 lines in the main scan, acquire MR signals only on 32 lines centered at the phase encoding quantity of zero in the F0 preparatory scan and fill the remaining 96 lines with zero in the F0 preparatory scan. While a period of time for acquiring MR signals in the F0 preparatory scan is reduced (shortened to a quarter as to the above example), the phase encoding number after zero filling is same as that of the main scan (128 lines for both as to the above example) by means of such data processing. A resolution being the same as that of the main scan can be thereby obtained for the F0 preparatory scan.

(3-2) Second Modification of First Embodiment

When a new main scan is performed for the same patient, imaging conditions of a previously performed main scan can be applied and edited so that imaging conditions are set for the new main scan in some cases. If imaging cross sections of the new main scan and the previous main scan are the same, situations in which banding artifacts appear are substantially the same, and thus an optimum center frequency F0$opt$ in the new main scan can be set identical to the optimum center frequency F0$opt$ in the previous main scan.

If the position or orientation of the imaging cross section in the new main scan is different from the imaging cross section in the previous main scan, though, the optimum center frequency F0$opt$ set for the previous main scan can no longer be said to be optimum, and a banding artifact may possibly interfere with the ROI.

Figure 9:
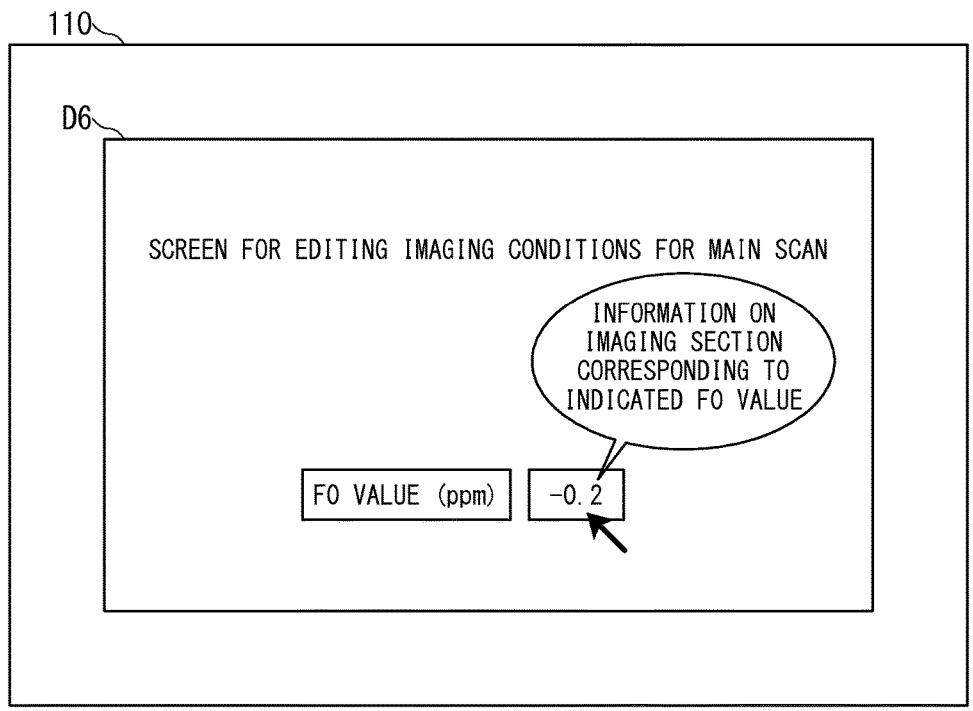
FIG. 9 illustrates an exemplary displayed image of a second modification of the first embodiment.

Thus, according to a second modification, information is indicated on a cross section image corresponding to an optimum center frequency F0$opt$ set for a previous main scan in editing imaging conditions for a new main scan. FIG. 9 illustrates an exemplary indication.

FIG. 9 illustrates only a portion related to the center frequency F0 in an imaging conditions editing screen D6 for editing imaging conditions for a previous main scan. Suppose that the optimum center frequency was "−0.2" ppm in imaging conditions for a previous main scan. It is supposed, when a cursor is shifted into this indication area, to indicate information related to an imaging cross section corresponding to the optimum center frequency in a balloon. The balloon indication enables an instantaneous decision on whether the imaging cross section in the new main scan and the imaging cross section corresponding to the optimum center frequency F0$opt$ to be applied are the same. If the imaging cross sections are the same, the previous optimum center frequency F0$opt$ can be applied. If they differ, a main scan performed by the use of the previous optimum center frequency F0$opt$ may probably be useless.

According to the second modification of the first embodiment, information is indicated on a cross section image corresponding to an optimum center frequency to be edited, so that a useless main scan can be prevented from being performed in this way.

(4) Second Embodiment

The first embodiment previously described discloses a method by which a user shifts a position of a banding artifact while changing the center frequency F0 so as to find out an optimum center frequency F0$opt$ causing no banding artifact interference in the ROI. According to the first embodiment, the center frequency F0 needs to be continuously changed until the optimum center frequency F0$opt$ is found out.

According to a second embodiment, on the other hand, determine an optimum center frequency (or a shift value with respect to the optimum center frequency) directly from a situation indicated in a preparatory image in which banding artifacts appear, and set the determined optimum center frequency F0$opt$ as a center frequency for a main scan at the first try.

Figure 10:
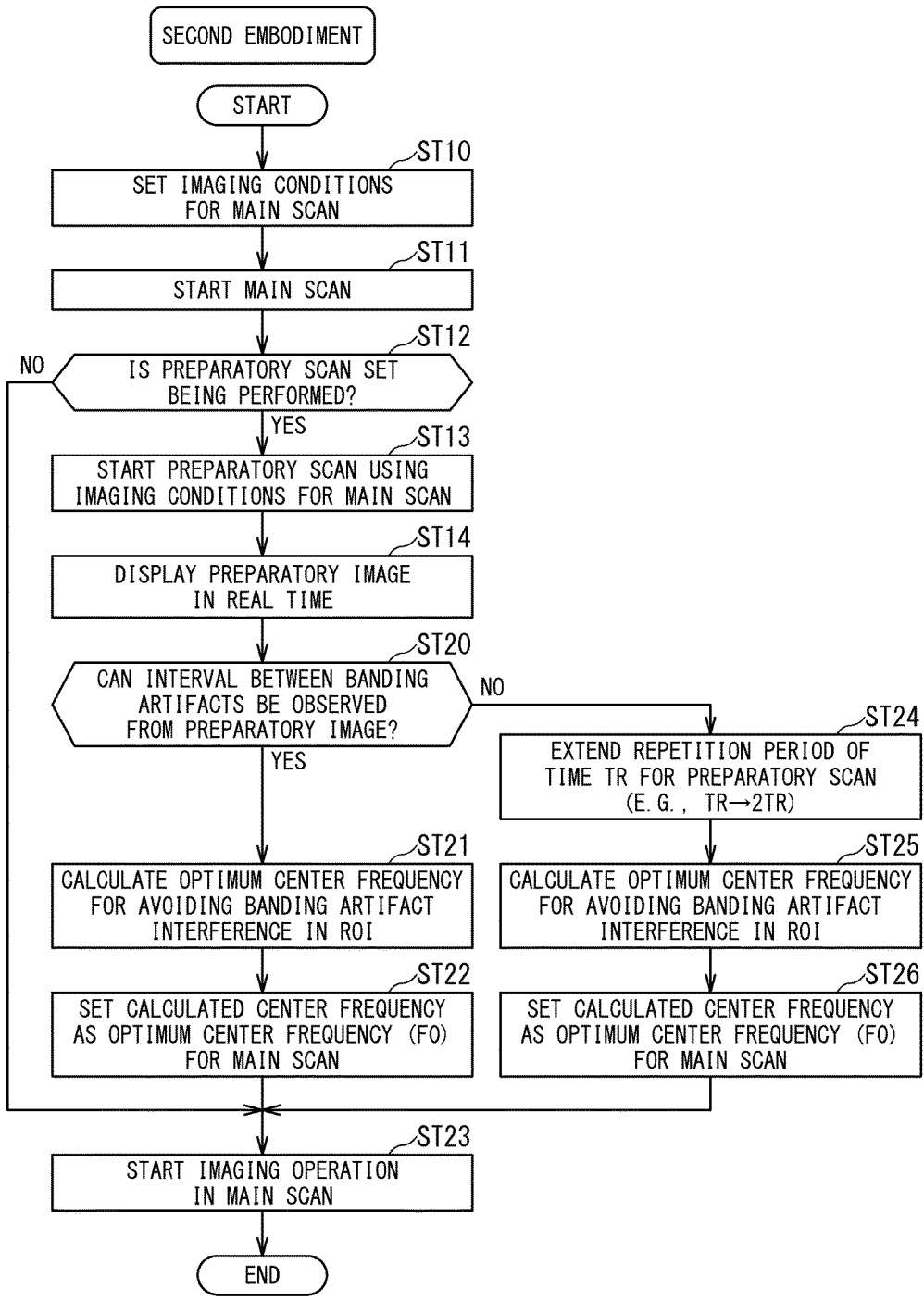
FIG. 10 is a flowchart which illustrates an exemplary operation of a magnetic resonance imaging apparatus of a second embodiment.

FIG. 10 is a flowchart which illustrates an exemplary operation of a magnetic resonance imaging apparatus 1 of the second embodiment. As steps ST10 (to set imaging conditions for a main scan) through ST14 (to indicate a preparatory image in real time) in FIG. 10 are the same as those of the first embodiment, their explanations are omitted.

While indicating a preparatory image in real time at the step ST14, decide at a step ST20 whether an interval between the banding artifacts can be observed from the preparatory image, that is, whether more than one banding artifact appears in the FOV. The decision is made, e.g., by a user who observes the preparatory image.

If an interval between the banding artifacts can be observed from the preparatory image, go forward to a step ST21 so as to calculate an optimum center frequency F0$opt$ for avoiding banding artifact interference in the ROI directly from the interval between the observed banding artifacts (step ST21).

Figure 11:
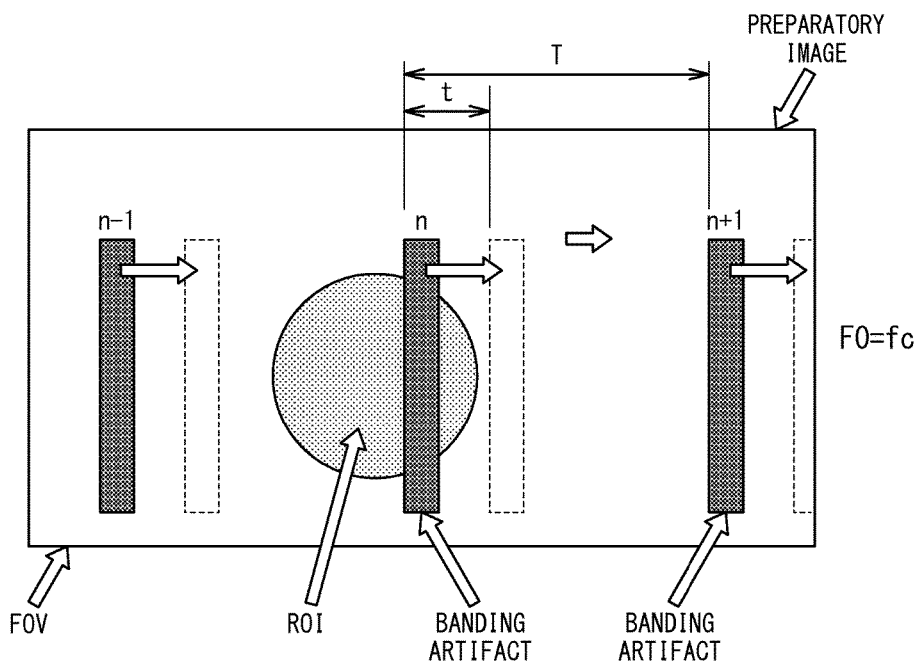
FIG. 11 illustrates a method for calculating an optimum center frequency from an interval between banding artifacts.

FIG. 11 illustrates a method for calculating an optimum center frequency F0$opt$ from an interval T between banding artifacts.

In general, a periodic feature n of banding artifacts is represented by following equations (1) and (2).

$$\phi = n \cdot (2\pi) = TR \cdot F0 \cdot (2\pi) \qquad \text{equation (1)}$$

$$\text{Therefore } n = TR \cdot F0 \qquad \text{equation (2)}$$

Symbols n, TR and F0 mentioned here are an integer, a repetition period of time of excitation pulses in the SSFP method (in seconds) and the center frequency (in hertz), respectively.

Suppose here that an interval between the banding artifacts appearing on the preparatory image is T and that the center frequency at that moment is fc, as depicted in an upper portion of FIG. 11. Suppose, then, that a distance (displacement) between the position of a banding artifact currently interfering with the ROI and the position (of a banding artifact indicated by an empty dashed rectangle in FIG. 11) not interfering with the ROI is t.

It is known from the equation (2) that, if the value (TR·F0) is increased or decreased one by one on an integer basis, the banding artifacts shift on an interval T by T basis. Further, it is known that, if the value (TR·F0) is changed by a quantity of one or below, the banding artifacts shift by a quantity smaller than the interval T. If the interval between the banding artifacts is T and the repetition period of time is TR, from these facts, a value fs of a shift of the center frequency required for shifting the banding artifacts by t is given by a next equation (3).

$$fs = (1/TR) \cdot (t/T) \quad \text{equation (3)}$$

That is, if the center frequency is shifted from the current center frequency fc by the value fs calculated according to the equation (3), the banding artifacts are satisfactorily shifted from the current positions of the banding artifacts indicated with black in FIG. 11 to the positions (of banding artifacts indicated by empty dashed rectangles in FIG. 11) not interfering with the ROI.

Note that the optimum center frequency F0opt after the shift is given as follows.

$$F0opt = fc + fs \quad \text{equation (4)}$$

The user can find out the interval T between the banding artifacts and the value t of the shift of the banding artifacts required for avoiding interference from the preparatory image, and further calculate, from the repetition period of time TR currently being set, the optimum center frequency F0opt according to the equations (3) and (4) (step ST21 in FIG. 10).

Then, set the calculated optimum center frequency F0opt as the optimum center frequency F0opt for the main scan (step ST22), and start an imaging operation in the main scan (step ST23).

The value to be inputted through the user interface can be a ppm value of the shift $((fs/fc) \cdot 10^6)$ instead of the optimum center frequency F0opt.

Figure 12:
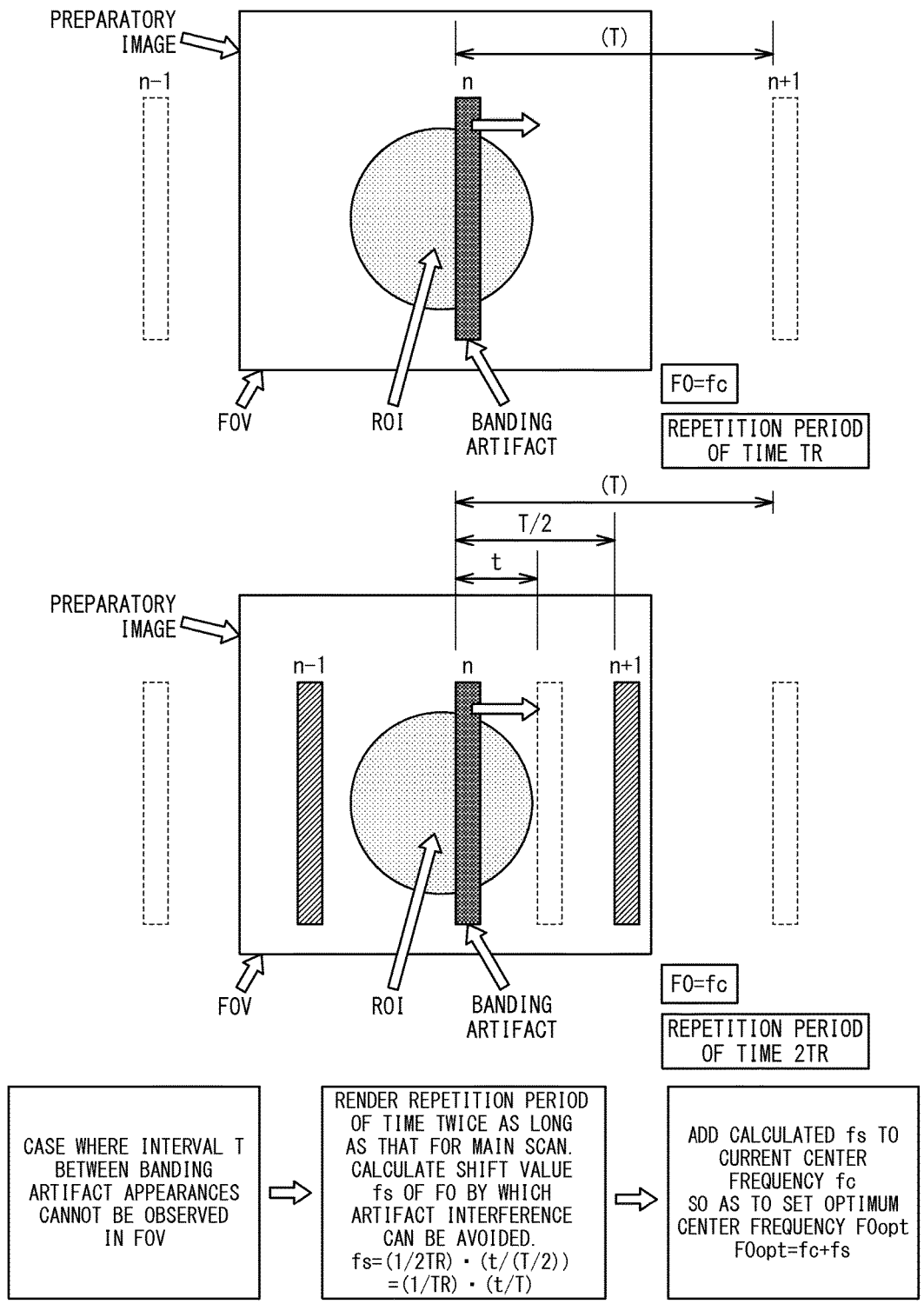
FIG. 12 illustrates a first method for calculating an optimum center frequency from an interval between banding artifacts after doubling a repetition period of time of an excitation pulse.

On the other hand, unless the interval between the banding artifacts can be observed from the preparatory image at the step ST20, i.e., if the interval between the banding artifacts is significantly large compared with the FOV as depicted in an upper portion of FIG. 12 and only one banding artifact appears in the FOV, go forward to a step ST24.

At the step ST24, change the current repetition period of time TR in the F0 preparatory scan by rendering TR, e.g., twice as long, i.e., 2TR and set the changed TR. If the repetition period of time TR is rendered longer, the interval between the banding artifacts becomes shorter. If, e.g., the interval between the banding artifacts is T when the repetition period of time is TR, the interval between the banding artifacts is (T/2) when the repetition period of time is 2TR as depicted in a middle portion of FIG. 12, and the interval between the banding artifacts can thereby be observed in the preparatory image (i.e., in the current FOV).

Then, find out a distance (displacement) t between the position of a banding artifact currently interfering with the ROI and the position (of a banding artifact indicated by a dashed rectangle in the middle portion of FIG. 12) not interfering with the ROI from the preparatory image depicted in the middle portion of FIG. 12, similarly as in FIG. 11. Then, substitute the interval between the banding artifacts (T/2) in the middle portion of FIG. 12 and the repetition period of time (2TR) for the equation (3), and then obtain the same result as the equation (3) as follows.

$$fs = (1/2TR) \cdot (t/(T/2)) \quad \text{equation (5)}$$
$$= (1/TR) \cdot (t/T)$$

At a step ST25, find out the shift value fs of the center frequency causing no banding artifact interference in the ROI on the basis of the equation (5), or calculate the optimum center frequency F0opt from the equation (4), and set the calculated optimum center frequency F0opt as the optimum center frequency F0opt for the main scan (step ST26).

Figure 13:
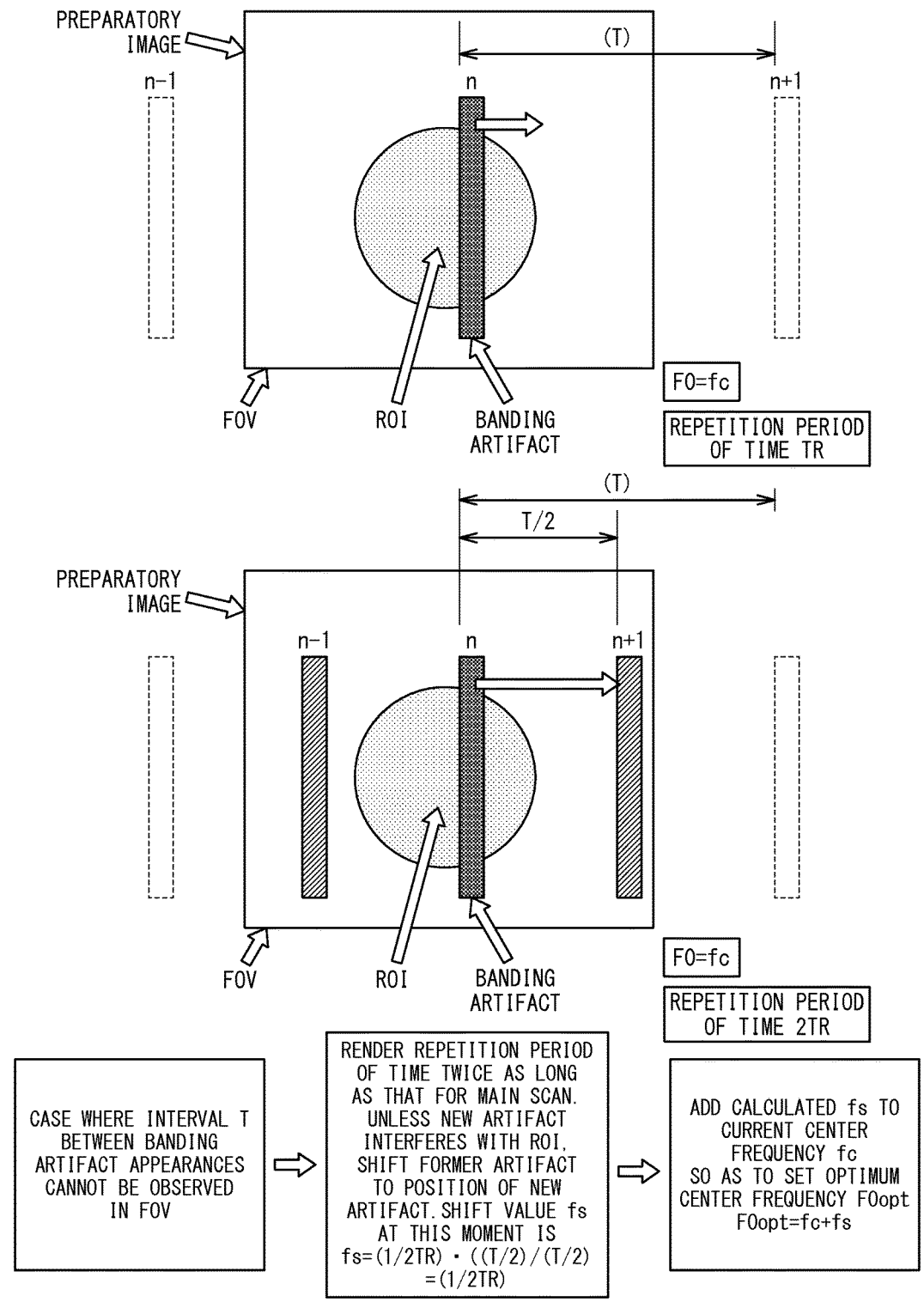
FIG. 13 illustrates a second method for calculating an optimum center frequency from an interval between banding artifacts after doubling a repetition period of time of an excitation pulse.

Further, when the repetition period of time is rendered (2TR) at the step ST24, new banding artifacts having an interval of (T/2) appear. Unless the new banding artifacts are not put on top of the ROI, banding artifact interference in the ROI can be avoided if the former banding artifacts are shifted to positions of the new banding artifacts, as depicted in FIG. 13.

If (T/2) is substituted for t in the equation (5), a shift value of the center frequency in this case is obtained. That is as follows.

$$fs = (1/2TR) \cdot ((T/2)/(T/2)) \quad \text{equation (6)}$$
$$= (1/2TR)$$

According to the magnetic resonance imaging apparatus 1 of the second embodiment, as described above, a user can obtain an optimum center frequency F0opt or a shift value fs to the optimum center frequency F0opt directly from the interval between banding artifacts appearing in the preparatory image, and can directly set the obtained value to the apparatus. Further, if the interval between banding artifacts cannot be found out directly from the preparatory image, it is practical as well to set the repetition period of time TR for the F0 preparatory scan twice as long (or even longer) so as to intentionally narrow the interval between the banding artifacts, and to find out the interval between the banding artifacts, then.

According to the magnetic resonance imaging apparatus 1 of the embodiment, an optimum F0 for avoiding banding artifacts can be efficiently determined without a significant operation load.

The embodiments of the invention having been explained are presented as exemplary only, and it is not intended to limit the scope of the invention. These embodiments can be practiced in other various forms, and can be variously omitted, replaced or changed within the gist of the invention. The inventions and their modifications are included in the scope and the gist of the invention, and in the inventions described in the claims and their equivalents as well.

What is claimed is:

1. A magnetic resonance imaging (MRI) apparatus comprising:
   an MRI system including at least one processor configured to
   set an imaging condition for a main scan to obtain a diagnostic image;
   accept a user input center frequency changeably inputted in real time;
   repeat a preparatory scan performed by use of the set imaging condition and the center frequency changeably inputted in real time and generate preparatory images in real time visibly depicting a banding artifact using the preparatory scan data acquired in the repeated preparatory scans;
   display the preparatory images in real time;
   change the center frequency according to a user operation via a user interface so as to change where the banding artifact appears, the optimum center frequency being set according to a user operation based on observation of the preparatory images; and perform the main scan by using the set optimum center frequency and the set imaging condition for the main scan to reconstruct the diagnostic image.

2. The magnetic resonance imaging apparatus according to claim 1, wherein both the main scan and the preparatory scan are performed using an SSFP (Steady State Free Precession) method.

3. The magnetic resonance imaging apparatus according to claim 1, wherein the imaging condition set for the main scan includes information on an imaging cross section image which is to be captured in the main scan, and an imaging cross section which is same as a cross section to be used for the main scan is included in the preparatory scan.

4. The magnetic resonance imaging apparatus according to claim 3, wherein, when the imaging cross section in the main scan includes a plurality of slices, a middle one of the slices is included in the preparatory scan, and when the imaging cross section in the main scan is a slab having a certain thickness, one slice corresponding to a middle position of the slab is included in the preparatory scan.

5. The magnetic resonance imaging apparatus according to claim 1, wherein the preparatory scan is automatically started according to a user operation to start the main scan after the imaging condition is set, and the main scan is automatically started when the optimum center frequency is set according to a user operation during the repeated preparatory scans.

6. The magnetic resonance imaging apparatus according to claim 1, wherein the set imaging condition for a main scan includes information on resolution in the main scan, and the preparatory scan is performed in such a way that resolution is rendered the same as the resolution in the main scan.

7. The magnetic resonance imaging apparatus according to claim 6, wherein the preparatory scan acquires a signal only in a specific range centered at a phase encoding quantity of zero, and complements zero for a range excepting the specific range to perform reconstruction processing.

8. The magnetic resonance imaging apparatus according to claim 1, wherein information on an imaging cross section in a main scan to be performed on the basis of an optimum center frequency having been previously set for acquisition of a prior diagnostic image is displayed on a user interface display.

9. The magnetic resonance imaging apparatus according to claim 1, wherein the optimum center frequency is set so that the banding artifact is put apart from what is to be observed.

10. A magnetic resonance imaging (MRI) apparatus comprising:

an MRI system including at least one processor configured to set an imaging condition for a main scan to obtain a diagnostic image;

repeat a preparatory scan performed by use of the set imaging condition, the preparatory scan generating preparatory images in real time visibly depicting a banding artifact using data acquired in the preparatory scans;

display the preparatory images in real time;

accept a user input shift value of a center frequency that a user has determined based on the banding artifact appearing on the displayed preparatory images;

add and/or subtract the user-inputted shift value of the center frequency to and/or from a center frequency corresponding to that used for generating the preparatory images used for determination of the shift value of the center frequency so as to obtain a new center frequency, the optimum center frequency being set to the new obtained center frequency; and perform the main scan using the set optimum center frequency and the imaging condition for the set main scan so as to reconstruct the diagnostic image.

11. The magnetic resonance imaging apparatus according to claim 10, wherein the imaging condition for the main scan includes a repetition period of time (TR) for an excitation pulse sequence, and the preparatory scan is performed with a repetition period of time (2TR) twice as long as the set repetition period of time.

* * * * *